US005099032A

United States Patent [19]

Tim-Wo Chu

[11] Patent Number: 5,099,032
[45] Date of Patent: * Mar. 24, 1992

[54] PROCESS FOR THE PREPARATION OF ENANTIOMERICALLY HOMOGENEOUS AMINOPYRROLIDINYL NAPHTHYRIDINE AND QUINOLONE CARBOXYLIC ACIDS.

[75] Inventor: Daniel Tim-Wo Chu, Vernon Hills, Ill.

[73] Assignee: Abbott Laboratories, Abbott Park, Ill.

[*] Notice: The portion of the term of this patent subsequent to Aug. 22, 2006 has been disclaimed.

[21] Appl. No.: 531,816

[22] Filed: Jun. 1, 1990

Related U.S. Application Data

[62] Division of Ser. No. 356,970, May 25, 1989, Pat. No. 4,956,475, which is a division of Ser. No. 167,058, Mar. 11, 1988, Pat. No. 4,859,776.

[51] Int. Cl.⁵ .............................. C07D 207/14
[52] U.S. Cl. .................................. 548/557; 546/123; 548/531; 548/539; 548/540; 548/557
[58] Field of Search ............... 548/557, 531, 539, 540

[56] References Cited

U.S. PATENT DOCUMENTS 4,785,119 11/1988 Hojo et al. ..................... 548/557

OTHER PUBLICATIONS

Brown et al., *J. Organic Chemistry*, 51, 4296–4298, 1986.

*Primary Examiner*—C. Warren Ivy
*Assistant Examiner*—James H. Turnipseed
*Attorney, Agent, or Firm*—Steven R. Crowley; Andreas M. Danckers

[57] ABSTRACT

A process for the preparation of enantiomerically homogeneous aminopyrrolidinyl naphthyridine carboxylic acids and quinolone carboxylic acids, and for the preparation of intermediates that are useful in the production of these carboxylic acids.

3 Claims, No Drawings

PROCESS FOR THE PREPARATION OF ENANTIOMERICALLY HOMOGENEOUS AMINOPYRROLIDINYL NAPHTHYRIDINE AND QUINOLONE CARBOXYLIC ACIDS.

This is a division of application Ser. No. 356,970, filed May 25, 1989, now U.S. Pat. No. 4,956,475 which is a division of application Ser. No. 167,058, filed Mar. 11, 1988 (now U.S. Pat. No. 4,859,776).

TECHNICAL FIELD

This invention relates to a new process for the preparation of enantiomerically homogeneous aminopyrrolidinyl naphthyridine carboxylic acids and quinolone carboxylic acids, particularly to (S)-7-(3-aminopyrrolidin-1-yl)-1-(o,p-difluorophenyl)-1,4-dihydro-6-fluoro-4-oxo-1,8-naphthyridine-3-carboxylic acid, to the preparation of intermediates that are useful in the preparation of these carboxylic acids, as well as to a novel azide reduction process for the reductive acetylation of an azido substituent.

BACKGROUND ART

Two molecules that possess identical chemical formulas with the same atoms bonded one to another but that differ in the manner that those atoms are arranged in space are referred to as stereoisomers. Stereoisomers that are mirror images of each other such that they are not superimposable one upon the other, because they have opposite configurations, are referred to as enantiomers. A mixture of equal parts of the two mirror image forms, or enantiomeric forms, is referred to as a racemic mixture.

Physiological activity has been shown to be closely related to the configuration of a molecule. For example, it is known that one enantiomeric form of adrenalin is over ten times more active in raising blood pressure than is the other form. Additionally, enzymes which catalyze chemical reactions in the body are frequently programmed to accept one enantiomeric form but not the other. 7-(Aminopyrrolidin-1-yl)naphthyridine carboxylic acids (Chu, U.S. Pat. No. 4,616,019, issued Oct. 7, 1986) and 7 (aminopyrrolidin 1-yl)quinolone carboxylic acids (Chu, U.S. Pat. No. 4,730,000, issued Mar. 8, 1988) are known to be antibacterial agents. A racemic mixture of 7 (3 aminopyrrolidin 1 yl)-1-(o,p difluorophenyl)-1,4-dihydro-6-fluoro-4-oxo-1,8-naphthyridine-3-carboxylic acid has been shown to exhibit antibacterial properties. J. Med. Chem., 29, 2363 (1986). A racemic mixture of 7-(3-aminopyrrolidin-1-yl)-1-(o,p difluorophenyl)-1,4-dihydro-6-fluoro 4-oxo-1,8-naphthyridine-3-carboxylic acid is prepared by Reaction Scheme I as illustrated below:

Reaction Scheme I

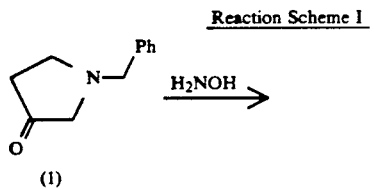

-continued
Reaction Scheme I

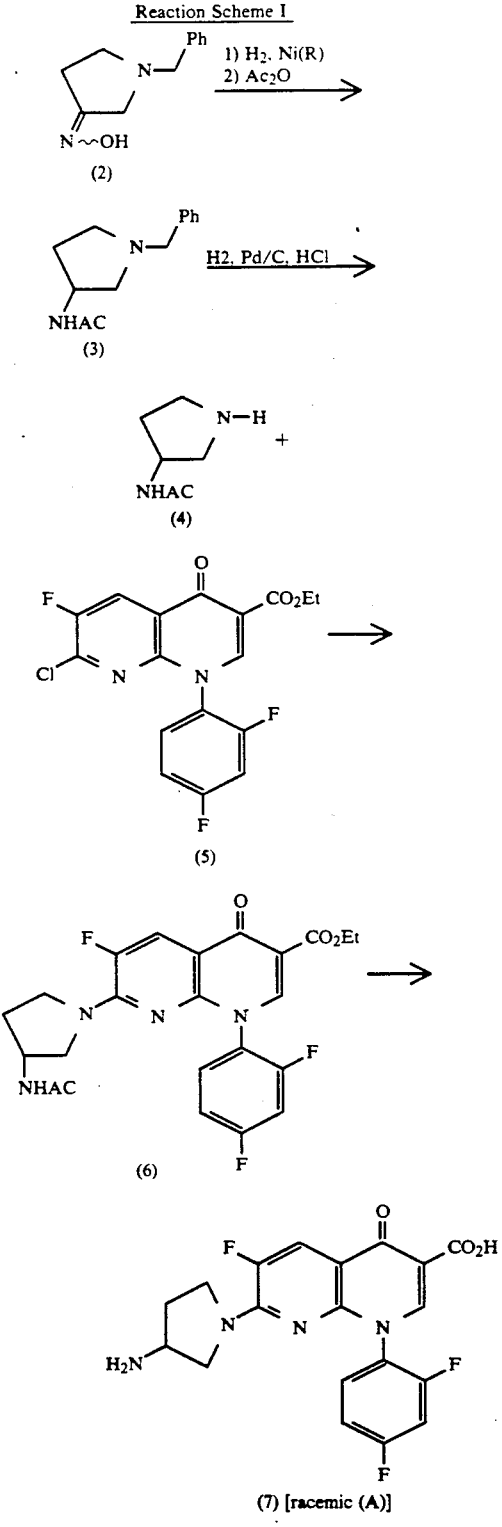

In Reaction Scheme I, the oxime (2) is reduced with Raney nickel and hydrogen which results in a racemic mixture having equal parts of the two enantiomeric forms of the molecule (3). This racemic intermediate will subsequently result in the production of a racemic mixture of (A). However, only one enantiomeric form of (A) may possess biological activity. Further, one enantiomeric form of this molecule may be capable of producing an undesirable side effect while the other enantiomeric form may be the form that exhibits antibacterial properties. It is therefore desirable to provide a process for the preparation of a specific enantiomeric form of 7-(3-aminopyrrolidin-1-yl)-1-(o,p-difluorophenyl)-1,4-dihydro-6-fluoro-4-oxo-1,8-naphthyridine-3-carboxylic acid.

As will be discussed in greater detail below, one alternative is to provide an azide rather than the oxime (2), reduce the azide to an amine, acetylate the amine, and thereafter remove the benzyl group to obtain (4). The reduction of an azide to an amine is a process that is widely used in organic synthesis because of the high stereoselectivity associated with the preparation of the precursor azide. Accordingly, several methods and reagents are known to reduce an azide to an amine. For example, catalytic hydrogenation [Mungall, J. Org. Chem., 40, 1659 (1975); and Corey, Synthesis, 590 (1975)], or lithium aluminum hydride [Hedayatullah, Tetrahedron Lett., 2455 (1975); Brimacombe, Carbohydr. Res., 3, 318 (1967); Bose, J. Org. Chem., 27, 2925 (1962); and Boyer, J. Am. Chem., 73, 5865 (1951)]. Other processes include $H_2S$/pyridine/$H_2O$ [Adachi, Synthesis, 45 (1977)]; transfer hydrogenation [Gartiser, Tetrahedron Lett., 24, 1609 (1984)]; $Ph_3P$/$NH_4OH$ [Vaulter, Tetrahedron Lett., 24. 763 (1983)]; $H_2$/Lindlar catalyst [Corey, Synthesis, 590 (1975); Cr(II)/H + [Kirk, J. Chem. Soc. Chem. Commun., 64 (1970); and Kondo, Tetrahedron, 29, 1801 (1973)]; as well as $Na_2S$/$Et_3N$/MeOH [Belinka, J. Org. Chem., 44, 4712 (1979)]. Most recently, there have been reports of procedures using stannous chloride/MeOH [Maiti, Tetrahedron Lett., 27, 1423 (1986)] and $NaBH_4$/THF/MeOH [Soai, Synthesis, 48 (1986)]. Although many reagents have been proposed, none have proven completely satisfactory because they either lack chemoselectivity or require vigorous reaction conditions to achieve the desired reduction of the azide.

DISCLOSURE OF THE INVENTION

It has now been discovered that (S)-7-(3-aminopyrrolidin-1-yl)-1-(o,p difluorophenyl)-1,4-dihydro-6-fluoro-4-oxo-1,8-naphthyridine3-carboxylic acid can be prepared according to Reaction Scheme II, illustrated below:

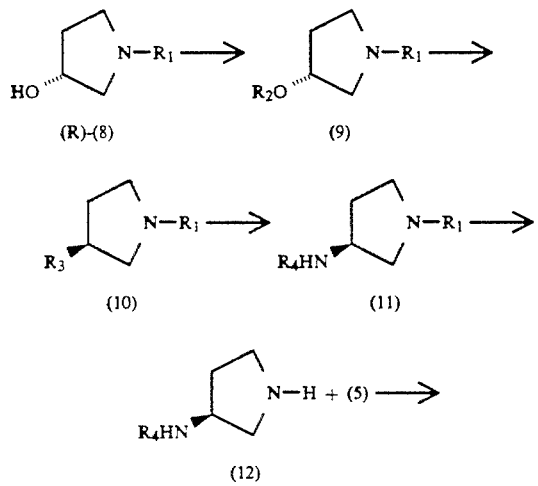

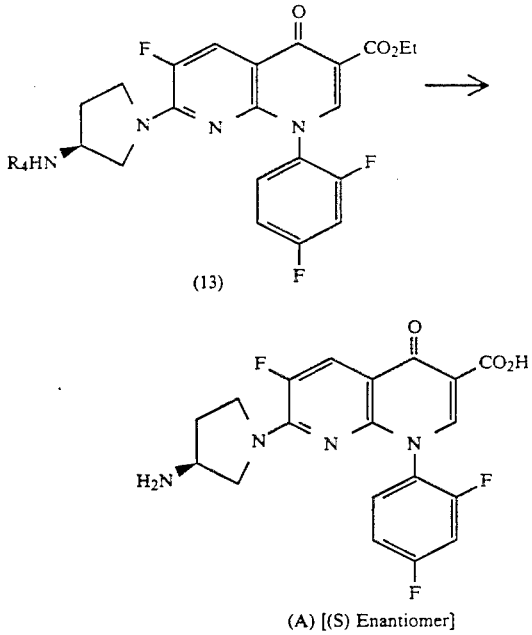

wherein $R_1$ is an N-1 protecting group such as benzyl, carbobenzyloxy, tert-butoxycabonyl, $C_1$ to $C_6$ alkanoyl, aroyl, or alkyl- or arylsulfonyl; $R_2$ is an activating group such as methansulfonyl, p-toluenesulfonyl, or trifluoromethanseulfonyl, which transform the hydroxyl group into a leaving group; $R_3$ is amino or a functional group which may be converted to an amine stereospecifically with retention of configuration, such as azido or nitro; and $R_4$ is a nitrogen protecting group that is selected to be stable under the conditions required to remove the nitrogen protecting group $R_1$. Therefore, $R_4$ can include benzyl, carbobenzyloxy, tert butoxycarbonyl, $C_1$ to $C_6$ alkanoyl, aroyl, or $C_1$ to $C_6$ alkyl- or arylsulfonyl, and in some cases arylmethyl, acetyl or hydrogen depending on the substituent employed for $R_1$. Preferably, $R_1$ is benzyl, $R_2$ is methanesulfonyl, $R_3$ is azide and $R_4$ is acetyl. Where $R_3$ is an azide, reductive acetylation of the azide (10) is preferably achieved with thioacetic acid to form the corresponding acetamide (11) in a single step.

The term "$C_1$ to $C_6$ alkyl" as used herein refers to straight or branched chain alkyl radicals containing from 1 to 6 carbon atoms.

The term "$C_1$ to $C_6$ alkanoyl" as used herein refers to $R_5CO$— wherein $R_5$ is $C_1$ to $C_6$ alkyl.

The term "aroyl" as used herein refers to $R_6CO$— wherein $R_6$ is phenyl or substituted phenyl wherein the phenyl ring is substituted with one, two or three substituents independently selected from halogen, loweralkyl, nitro and alkoxy.

The term "halogen" as used herein refers to fluoro, bromo, chloro or iodo.

The term "$C_1$ to $C_6$ alkylsulfonyl" as used herein refers to $R_7SO_2$— wherein $R_7$ is $C_1$ to $C_6$ alkyl.

The term "arylsulfonyl" as used herein refers to $R_8SO_2$— wherein $R_8$ is phenyl or p-tolyl.

The term "alkoxy" as used herein refers to $R_9O$— wherein $R_9$ is a loweralkyl radical.

The term "leaving group" as used herein refers to chloro, bromo, iodo, or sulfonate esters such as mesylate, triflate, tosylate and the like.

The term "N-1 protecting group" or "nitrogen protecting group" as used herein refers to those groups intended to protect an amino group against undesirable reactions during synthetic procedures and includes but is not limited to benzyl, acetyl, pivaloyl, tert-butoxycarbonyl, carbobenzyloxy or benzoyl.

As used herein, the term "pharmaceutically acceptable salts" means the nontoxic acid addition or alkaline earth metal salts of the compound of formula (A). These salts can be prepared in situ during the final isolation and purification of the compound of formula (A), or by separately reacting the base or acid functions with a suitable organic or inorganic acid or base, respectively. Representative acid addition salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, glucoheptonate, lactobionate, lauryl sulfate salts and the like. Representative alkali metal or alkaline earth metal salts include the sodium, calcium, potassium and magnesium salts, and the like.

In accordance with the foregoing Reaction Scheme II, an N-1 protected (R)-3-hydroxypyrrolidine intermediate (R)-(8) is utilized to prepare the enantiomerically homogeneous (S) -b 7-(3-aminopyrrolidin-1-yl)-1-(o,p-difluorophenyl)-1,4-dihydro-6-fluoro-4-oxo-1,8-naphthyridine-3-carboxylic acid (A). For example, the enantiomerically homogeneous alcohol (R)-(8), where the N-1 protecting group $R_1$ is benzyl, is reacted with a sulfonating reagent such as an alkyl- or arylsulfonyl chloride or an alkyl- or arylsulfonic acid anhydride to obtain a sulfonate ester (9). The reaction takes place in an organic solvent such as dimethylformamide (DMF), dichloromethane, tetrahydrofuran (THF), or pyridine in the presence of a base such as triethylamine or 1,8-diazabicyclo[5.4.0]undec-7-ene (DBU). The temperature range is approximately −30 to 60 degrees Celsius (C.). Preferably, (R)-(8), is reacted with methanesulfonyl chloride in dichloromethane and in the presence of the base triethylamine to obtain the sulfonate ester (9), where $R_2$ is methanesulfonyl. This reaction proceeds acceptably at room temperature but is preferably run at approximately 25 degrees C.

The sulfonate ester group is displaced with a nitrogen nucleophile, such as an ammonia, phthalimide or an azide reagent to obtain (10). Azide reagents can include, among others, sodium azide, lithium azide, or tetra-n-butylammonium azide in an organic solvent, such as acetonitrile, DMF, or THF. The reaction can take place within a temperature range of from approximately room temperature to 125 degrees C. Preferably, the sulfonate ester (9) is reacted with tetra n-butylammonium azide in acetonitrile to provide the azide (10).

The nitrogen nucleophile is then transformed to provide an amine (11). Where the nitrogen nucleophile is an azide, the transformation can be accomplished with hydrogen and a metallic catalyst such as platinum on carbon (Pt/C) or palladium on carbon (Pd/C) in an organic solvent, such as methanol or ethanol to provide the amine (11). On the other hand, a hydride reagent, such as lithium aluminum hydride or lithium borohydride can be used to reduce the azide group. The resulting amine (11) is then acylated with a carboxylic acid anhydride, preferably acetic anhydride, and the $R_1$ group is cleaved to obtain (12), where $R_4$ is acetyl.

The acylated compound (12) is subsequently reacted to form (A) in a process similar to that found in the reaction illustrated in Reaction Scheme I. In other words, the compound (12), in this case (S)-3-acetamidopyrrolidine, is reacted with 7-chloro-1-(o,p-difluorophenyl)-1,4-dihydro-6-fluoro-4-oxo-1,8-naphthyridine-3-carboxylic acid or its ethyl ester (5) to obtain (13) after which the ester and amide groups are hydrolyzed to obtain (S)-7-(3-aminopyrrolidin-1-yl)-1-(o,p-difluorophenyl)-1,4-dihydro-6-fluoro-4-oxo-1,8-naphthyridine-3-carboxylic acid (A).

Alternatively, the azide (10) can be directly converted to an acetamide (11). It has now been discovered that azides will react with thiolacetic acid to provide chemoselective reduction of the azide with an accompanying acetylation to give the corresponding acetamide. The reductive acetylation of azides with thiolacetic acid has been found to have general utility for the reduction of functionally diverse azides. Further, the reaction occurs in the presence of a wide variety of functional groups, such as t-butoxycarbonyl and benzyl protecting groups, methyl esters, olefins, carboxylic esters, and methanesulfonate ester.

The reaction is rapid and generally occurs under mild conditions. For example, the reaction takes place at room temperature, with or without a solvent, to reach completion within a matter of minutes. Further, the reaction is extremely convenient to carry out and is accomplished by simply stirring the azide with thiolacetic acid. Thereafter, the reaction mixture can be concentrated with a rotary evaporator and, if desired, further purified by flash column chromatography.

Additionally, the reductive acetylation of azides with thiolacetic acid is advantageous with molecules that possess functional groups that were previously thought to be incompatible with a free amine. As seen in Reaction Scheme III below, treatment of the azido mesylate (14) with hydrogen and metal catalyst such as palladium in the presence of methanol, results in the reduction of the azide and subsequent intramolecular cyclization to yield the bicyclic amine (15). This cyclization occurs spontaneously and no amino mesylate is obtained. However, treatment of (14) with thiolacetic acid results in the acetamido mesylate (16). It is believed that the acetylation occurs so rapidly that the amine is trapped before intramolecular displacement can occur.

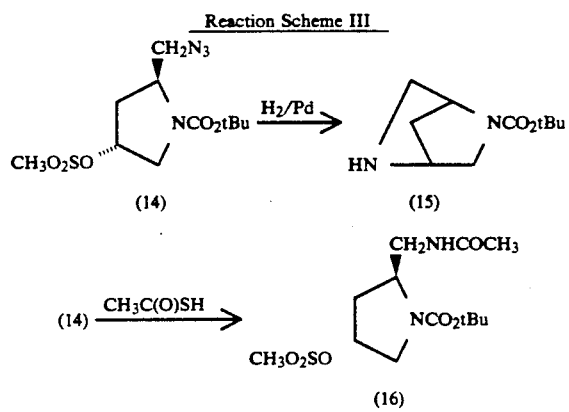

Reaction Scheme III

As illustrated in Reaction Scheme IV below, the starting material (11) can be prepared by hydroborating N-benzyl-3-pyrroline (17) with diisocamphenylborane to form an organoborane complex. Brown, J. Org. Chem., 51, 4296-4298 (1986). In this case, the organoborane complex is then reacted with $NH_2Cl$ (Brown, J. Am. Chem. Soc., 86, 3565 (1964)) to provide (18) in optically active form. The product (18) is therefore treated, as discussed above, to form the starting material (11) ($R_4=Ac$).

Reaction Scheme IV

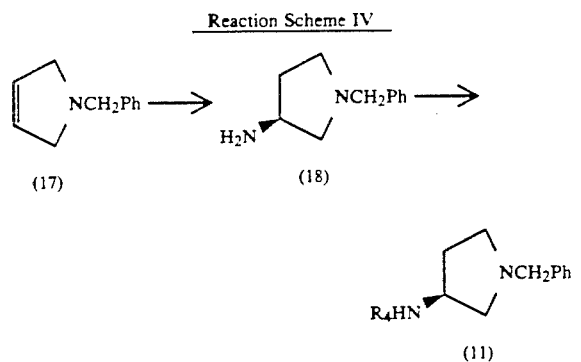

The differences in vivo antibacterial activity of racemic (R,S) compound (A) versus the (S) enantiomeric form of compound (A) are shown in Table I.

TABLE I

| POTENCY OF (A) IN MOUSE PROTECTION TESTS | | | |
|---|---|---|---|
| | | $ED_{50}$ (mg/kg/day) | |
| Organism | Compound | Subcutaneous | Oral |
| E. Coli Juhl | (R,S)-(A) | 0.3 | 1.2 |
| | (S)-(A) | 0.2 | 0.8 |
| P. Aeruginosa 5007 | (R,S)-(A) | >20 | 16.0 |
| | (S)-(A) | 8.6 | 12.1 |
| S. Aureus NCTC 10649 | (R,S)-(A) | 0.4 | 1.0 |
| | (S)-(A) | 0.4 | 0.8 |

The foregoing may be better understood from the following examples, which are presented for the purposes of illustration and are not intended to limit the scope of the inventive concepts. As used in the following examples, the references to compounds, such as (1), (2), (3), etc. and to substituents, such as R, $R_1$, $R_2$, etc., refer to the corresponding compounds and substituents in the foregoing reaction schemes.

EXAMPLE 1

(3S)-3-Acetamidopyrrolidine (12)

(a) Under a nitrogen atmosphere, 3.8 mL (6.1 g, 60.8 mmol) of methanesulfonyl chloride was slowly added to a solution of 4.3 g (24.3 mmol) of an N-1 protected (R)-(8) (J. Org. Chem. 51 4298 (1986)), where $R_1$ is benzyl, 8 mL of dichloromethane, and 8.5 mL (6.1 g, 60.8 mmol) of triethylamine. The solution was stirred at room temperature for approximately 16 hours after which the reaction mixture was diluted with dichloromethane and washed with saturated aqueous sodium bicarbonate and brine. The dichloromethane solution was dried (sodium sulfate) and concentrated with a rotary evaporator. The crude product was then purified by flash column chromatography utilizing 4:1 ethyl acetate/hexanes as eluant to obtain 3.3 g of the sulfonate ester (9), where $R_1$ is benzyl and $R_2$ is $SO_2CH_3$, as a yellow oil. $^1H$ NMR ($CDCL_3$): 2.10 (m, 1H), 2.30 (m, 1H), 2.50 (m, 1H), 2.75-2.90 (complex m, 3H), 3.00 (s, 3H), 3.62 (d, 1H, J=12.6 Hz), 3.68 (d, 1H, J=13.5 Hz), 5.20 (m, 1H), 7.30 (m, 5H).

(b) Under a nitrogen atmosphere, 7.5 g (26.4 mmol) of tetra N-butylammonium azide was added to a solution of 3.2 g (12.5 mmol) of the sulfonate ester (9) and 4 mL of acetonitrile. The solution was heated at approximately 65 degrees C. for 3 hours. The reaction mixture was then diluted with ether, washed with saturated aqueous sodium bicarbonate, dried, and concentrated with a rotary evaporator. The crude material was purified by flash column chromatography as above to obtain 2.29 g of (10), where $R_1$ is benzyl and $R_3$ is azido, as a colorless oil. $^1H$ NMR ($CDC_3$) 1.90 (m, 1H), 2.20 (m, 1H), 2.46 (m, 1H), 2.70 (complex m, 3H), 3.60 (d, 1H, J=12 Hz), 3.68 (d, 1H, J=13.5 Hz), 3.95 (m, 1H), 7.35 (m, 5H).

(c) Under a nitrogen atmosphere, a solution of 216 mg (1.07 mmol) of the azide (10), and 0.85 mL (0.9 g, 11 mmol) of thiolacetic acid was stirred at room temperature for approximately 5 hours and concentrated with a rotary evaporator. The crude material was subjected to flash column chromatography, increasing the polarity of the eluant from chloroform to 1:9 methanol/chloroform, to obtain (11), where $R_4$ is acetyl and $R_1$ is benzyl, as an oil. $^1H$ NMR ($CDCl_3$): 1.60 (m, 1H), 1.94 (s, 3H), 2.25 (m, 2H), 2.53 (dd, 1H, J=6, 10.5 Hz), 2.61 (dd, 1H, J=3, 10.5 Hz), 2.85 (m, 1H), 3.59 (s, 2H), 4.45 (m, 1H), 5.95 (bd, NH, J=6 Hz), 7.30 (m, 5H). The oil was dissolved in methanol and 50 mg of 20% Pd/C was added to the solution. The mixture was then placed under 4 atm of hydrogen for 24 hours. An additional 0.46 g 20% Pd/c was added to the system during this time. The catalyst was filtered out and the solvent was removed with a rotary evaporator to yield 130 mg of (12), where $R_4$ is acetyl, as a yellow oil. $^1H$ NMR ($CDC_{13}$) 1.67 (m, 1H), 1.97 (s, 3H), 2.16 (m, 1H), 2.85 (dd, 1H, J=3, 11 Hz), 2.96 (m, 1H), 3.11 (m, 2H), 3.48 (s, 1H), 4.41 (m, 1H), 6.26 (bs, 1H).

An alternate preparation of (3S)-3-acetamidopyrrolidine (12) began by repeating steps (a) and (b) as described above. However, instead of reducing the product (10) with thiolacetic acid, the reduction was accomplished with hydrogen in the presence of a platinum catalyst to obtain the amine (11). The amine was thereafter acylated with acetic anhydride and the $R_1$ group was cleaved as described above to obtain (12), where $R_4$ is acetyl.

A second alternate preparation of (3S)-3-acetamidopyrrolidine (12) involves repeating steps (a)-(c) described above, but replacing benzyl as the N-1 protecting group $R_1$ with a tert butoxycarbonyl N-1 protecting group. The tert butoxycarbonyl protecting group is removed under acidic conditions to obtain (12), where $R_4$ is acetyl.

EXAMPLE 2

(S)-7-(3-Aminopyrrolidin-1-yl)-1-(o,p-difluorophenyl)-1,4-dihydro-6-fluoro-4-oxo-1,8-naphthyridine-3-carboxylic Acid (A) Hydrochloride (a) Under a nitrogen atmosphere, 430 mg (1.13 mmol) of (5) was added to a solution of 120 mg (0.94 mmol) of the product (12) from Example 1, 0.3 mL of pyridine, and 0.17 mL (120 mg, 1.2 mmol) of triethylamine. J. Med. Chem., 29, 2363 (1986). The solution was heated at approximately 65 degrees C. for 21 hours to allow the reaction to come to completion before concentrating with a rotary evaporator. The crude material was purified by subjecting the product to flash column chromatography, gradually increasing the polarity of the eluant from chloroform to 5% methanol/chloroform, to obtain 343 mg of (13) as an orange solid (mp 240–243 degrees C.).

(b) Under a nitrogen atmosphere, 9.5 mL of a 1M aqueous sodium hydroxide solution was added to a suspension of 223 mg (2.48 mmol) of the product (13) from step (a) and 3 mL of THF. The reaction mixture was heated at approximately 65 degrees C. for 2 hours before being concentrated with a rotary evaporator.

(c) The residue from step (b) was suspended in 6M aqueous hydrochloric acid and heated to reflux (110 degrees C). The mixture was then cooled and concentrated. Thereafter, H$_2$O was added to the concentrated mixture resulting in an off-white solid (A) hydrochloride which was collected and dried in a vacuum oven yielding 101 mg of product. 1 H NMR (dmso-d$_6$) 2–3.9 (complex), 7.38 (m,1H), 7.57 (m,1H), 7.83 (m,1H), 8.23 (d,1H,J=14), 8.83 (s,1H).

EXAMPLE 3

[(S)-(1-Methoxy-1-phenyl 1-trifluoromethyl)methyl] Amide of (S)3-Amino-1-benzylpyrrolidine (a) To a solution of 35 mg (0.17 mmol) of the product 10, where R$_1$ is benzyl and R$_3$ is azido, in 15 mL of methanol was added 18 mg of 5% Pt/C and the mixture was placed under 4 atm of hydrogen. The catalyst was removed by filtration and the filtrate was concentrated with a rotary evaporator to obtain a yellow oil.

(b) To a solution of the oil from step (a) and 0.05 mL of pyridine was added 0.05 mL (35 mg, 0.35 mmol) of triethylamine and 0.05 mL (68 mg, 0.27 mmol) of (S)-(1-Methoxy-1-phenyl-1-trifluoromethyl)methyl acyl chloride. The reaction mixture was stirred under nitrogen at room temperature for approximately 8 hours, diluted with ether, and washed with saturated aqueous sodium bicarbonate and brine. The ether solution was then dried and concentrated with a rotary evaporator before being purified by flash column chromatography to obtain the [(S)-(1-Methoxy-1-phenyl-1-trifluoromethyl)-methyl]Amide of (S)-3-Amino-1-benzylpyrrolidine as a yellow oil. $^{19}$F NMR 8.236 ppm (internal standard trifluoroethanol). This NMR data indicates that the (S)-3-amino-benzylpyrrolidine obtained in step (a) is enantiomerically pure.

EXAMPLE 4

[(S)-(1-Methoxy-1-phenyl-1-trifluoromethyl)methyl] Amide of (R)3-Amino-1-benzylpyrrolidine The corresponding amide of (R)-3-amino-1-benzyl pyrrolidine can be prepared according to Example 3 by simply substituting one enantiomeric form of the starting material (10) with the opposite enantiomeric form.

EXAMPLE 5

(2S,4S)-4-Acetamido-1-t-butoxycarbonyl-2-methylpyrrolidine

Under a nitrogen atmosphere, 0.27 mL (280 mg, 3.7 mmol) of thiolacetic acid was added to 210 mg (0.93 mmol) of (2S,4S)-4-azido-1t-butoxycarbonyl-2-methyl-pyrrolidine. The reaction mixture was stirred at room temperature for approximately four hours and concentrated with a rotary evaporator. The resulting oil was subjected to flash column chromatography using 1:1 ethyl acetate/hexane followed by ethyl acetate as eluant to obtain 190 mg of (2S,4S)-4-acetamido-1-t-butoxycarbonyl-2-methylpyrrolidine (84% yield) as a yellow oil which solidified on standing. Recrystallization of a small sample from hexanes provided a white solid, mp 108–110 degrees C. The material thus obtained was found to be identical to the material obtained by a two-step procedure that provides for the hydrogenation of (2S,4S)-4-azido-1-t-butoxycarbonyl-2-methylpyrrolidine with hydrogen and Pd/C followed by a separate acetylation step utilizing acetic anhydride.

EXAMPLE 6

Benzylacetamide

Under a nitrogen atmosphere, 1.2 mL (1.3 g, 17.2 mmol) of thiolacetic acid was added to 570 mg (4.3 mmol) of benzyl azide. The reaction mixture was stirred at room temperature for approximately one hour and the thioacetic acid was removed with a rotary evaporator. The resulting oil was subjected to flash column chromatography using 1:1 ether/pentane followed by ether as eluant to obtain 580 mg of benzylacetamide (91% yield) as a white crystalline solid, mp 58–60 degrees C.

Alternatively, benzylacetamide was prepared according to the following procedure. Under a nitrogen atmosphere, 1.4 mL (1.5 g, 20 mmol) of thiolacetic acid was added to 0.54 mL (535 mg, 5 mmol) of benzylamine. A precipitate formed immediately. The thiolacetic acid was removed with a rotary evaporator to obtain 740 mg of benzylacetamide as a yellow solid. Recrystallization of the product from hexanes provided 690 mg (92% yield) of benzylacetamide. The physical and spectral properties of the material thus obtained were identical with those of the product obtained upon treatment of benzyl azide with thiolacetic acid as described in Example 7. The physical and spectral properties of the material obtained in this manner were identical with those of the product obtained upon treatment of benzylazide with thiolacetic acid.

EXAMPLE 7

In the fashion described in Examples 6 through 8, and corresponding to the transformation of (10) wherein R$_3$ is azide into (11) wherein R$_4$ is acetyl, the azide compounds listed in Table II were reacted with four to ten mole equivalents of thiolacetic acid. The resulting acetamide was concentrated with a rotary evaporator before being purified by flash column chromatography.

TABLE II

| Azide | | % Yield of Acetamide | mp |
|---|---|---|---|
| (1) | 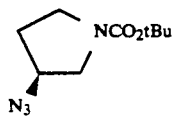 | 77 | oil |
| (2) | 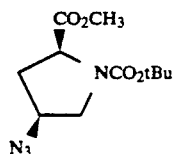 | 92 | 62–64 degrees C. |
| (3) | CH$_3$(CH$_2$)$_6$N$_3$ | 77 | oil |

TABLE II-continued

| Azide | % Yield of Acetamide | mp |
|---|---|---|
| (4) cyclohexyl-N₃ | 65 | 104 degrees C. |
| (5) styryl-N₃ | 73 | 88-90 degrees C. |
| (6) [pyrrolidine with CH₂N₃, NCO₂tBu, OSO₂CH₃] | 70 | oil |

It will be understood that various changes and modifications can be made in the details of the procedure to adapt it to various conditions without departing from the spirit of the invention, especially as defined in the following claims:

What is claimed is:

1. A process for the preparation of the enantiomerically pure (S) form of a compound of the formula:

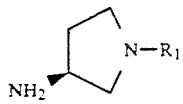

wherein $R_1$ is hydrogen benzyl, carbobenzyloxy, tert-butyloxycarbonyl, $C_1$ to $C_6$ alkanoyl, aroyl, $C_1$ to $C_6$ alkylsulfonyl or arylsulfonyl, comprising (a) transforming the hydroxyl group of the enantiomerically pure (R) form of a compound of the formula

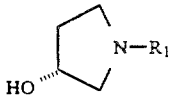

into a leaving group;

(b) introducing a nitrogen containing substituent by displacing the leaving group with a nitrogen nucleophile that is a precursor to an amino group; and (c) converting the nitrogen nucleophile to an amino group.

2. The process of claim 1 wherein the leaving group is a sulfonate ester.

3. The process of claim 1 wherein the nitrogen nucleophile is an azide, phthalimide, nitro or ammonia reagent.

* * * * *